United States Patent
Griffin

Patent Number: 5,812,681
Date of Patent: Sep. 22, 1998

[54] ARTIFICIAL LARYNX WITH FREQUENCY CONTROL

[76] Inventor: Clifford J. Griffin, 27636 Ynez Rd., Suite L7199, Temecula, Calif. 92591

[21] Appl. No.: 846,560

[22] Filed: Apr. 25, 1997

Related U.S. Application Data

[63] Continuation of Ser. No. 550,172, Oct. 30, 1995, abandoned.

[51] Int. Cl.[6] .......................................................... A61F 2/20
[52] U.S. Cl. .................................................. 381/70; 623/9
[58] Field of Search .......................... 381/70, 123; 623/9

[56] References Cited

U.S. PATENT DOCUMENTS

| | | | |
|---|---|---|---|
| 3,066,186 | 11/1962 | Trammell | 381/70 |
| 4,612,664 | 9/1986 | Walsh et al. | 381/70 |
| 4,726,066 | 2/1988 | Bloomfield, III | 381/70 |

Primary Examiner—Curtis A. Kuntz
Assistant Examiner—Ping W. Lee
Attorney, Agent, or Firm—Loyal Hanson

[57] ABSTRACT

An artificial larynx of the type having a case and a battery-powered, tone-producing, electrical circuit within the case, includes control components for enabling a user to turn on the circuit and vary the frequency of the tone. The turn-on control components include a switch having a switch actuator and a pushbutton or other suitable depressor component, while the frequency-control components include a pressure-sensitive resistor (PSR) electrically connected in the circuit and physically disposed intermediate the depressor component and the switch actuator. The PSR is electrically connected in the circuit so that the frequency of the tone varies when force is applied to the PSR, and it is physically disposed intermediate the depressor component and the switch actuator so that pressing the depressor component applies force to the switch actuator and the PSR simultaneously, thereby enabling the user to turn on the electrical circuit and vary the frequency of the tone by operation of just the one depressor component. One embodiment includes remote volume control capabilities using an infrared or other suitable signal encoded with volume control information derived from a pressure sensor placed proximate the users throat where the user exhales (e.g. a stoma).

9 Claims, 3 Drawing Sheets

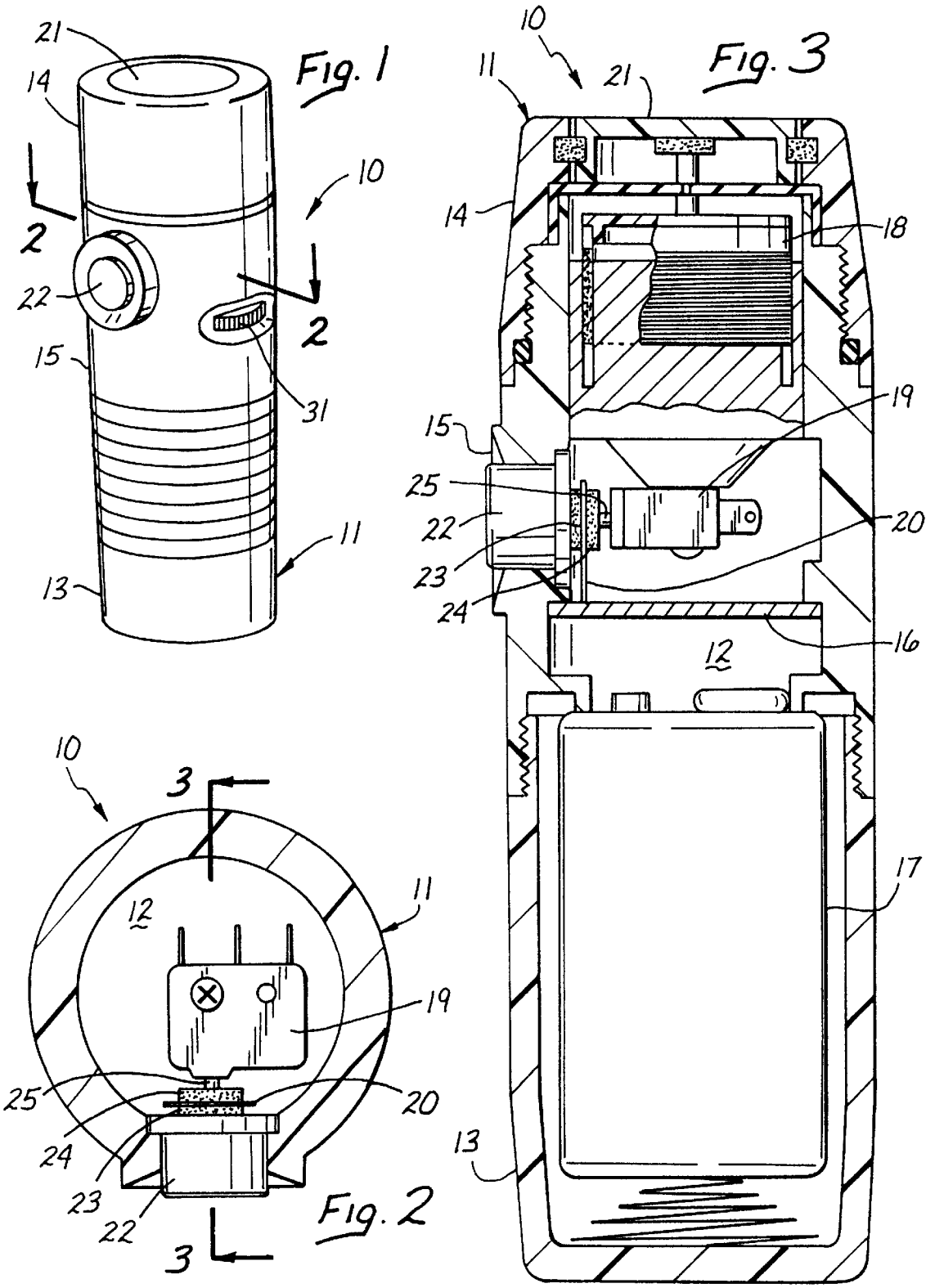

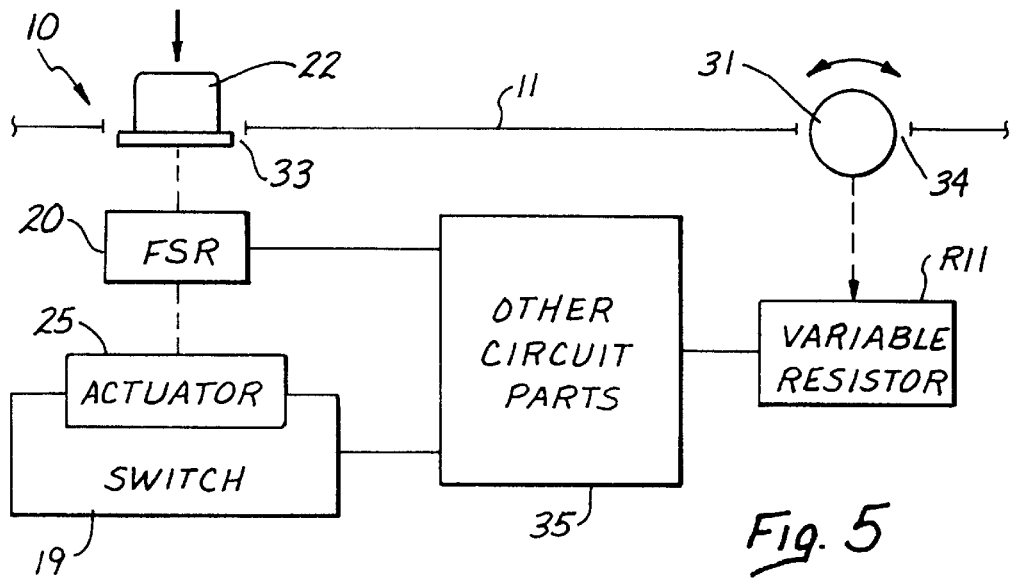
Fig. 5
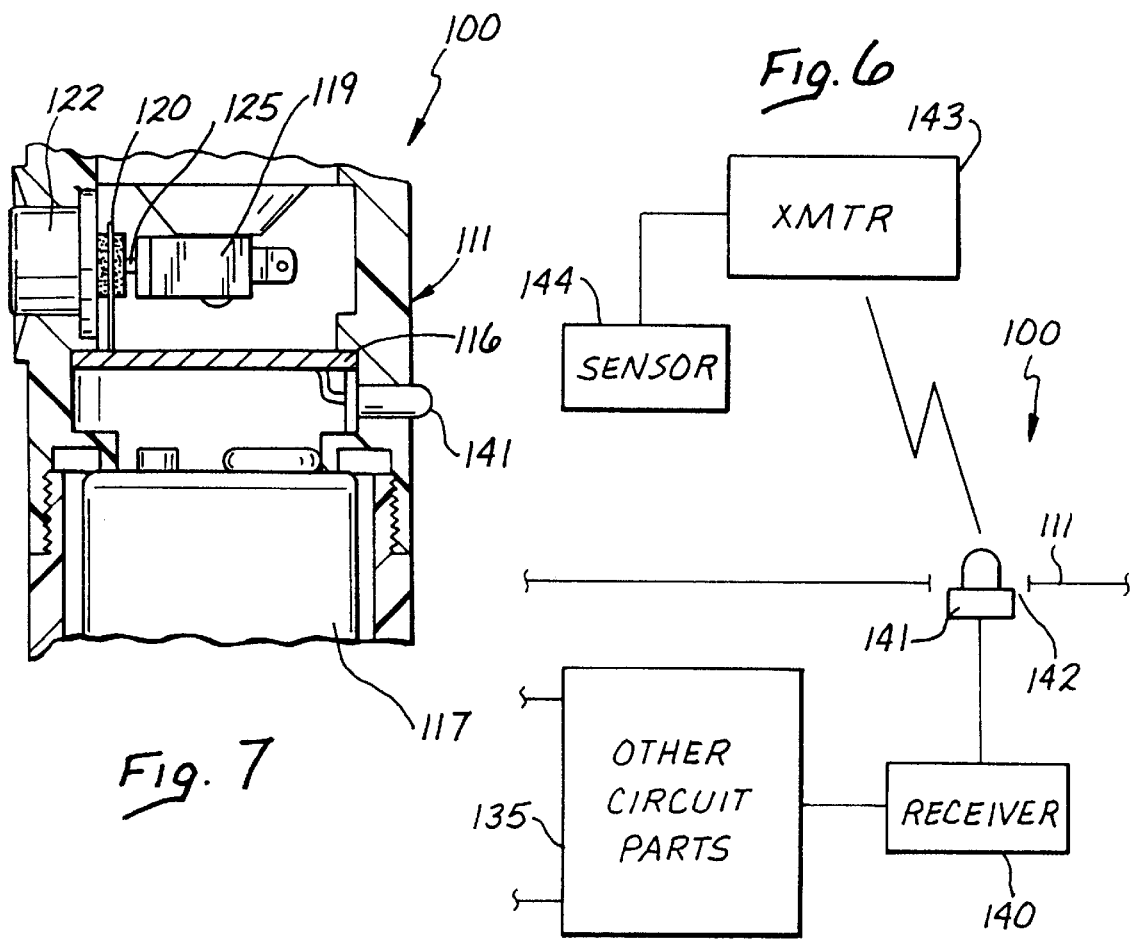
Fig. 7
Fig. 6

ARTIFICIAL LARYNX WITH FREQUENCY CONTROL

CROSS-REFERENCE TO RELATED APPLICATIONS

This application is a continuation of the U.S. patent application naming the same inventor that was assigned Ser. No. 08/550,172 and an Oct. 30, 1995 filing date now abandoned.

BACKGROUND OF THE INVENTION

1. Technical Field.

This invention relates generally to the mechanical and electromechanical speech aids commonly referred to generically as artificial larynxes, and more particularly to an electrically-powered artificial larynx having frequency change capabilities.

2. Description of Related Art.

An artificial larynx with frequency change capabilities can help a user produce the intonation desired for comprehensible, natural-sounding speech far better than its monotone counterparts. But some existing designs have drawbacks that render them ineffective. Ergonomic aspects need improvement.

To focus on that problem, first recall that persons without normal use of their vocal chords or larynx often use an artificial larynx to speak. The artificial larynx produces a tone having a fundamental frequency in the speech range of the average human voice, and the user introduces this artificially generated tone into a resonant speech cavity (i.e., the mouth, nose, or pharynx). To speak, the user modulates the tone by varying the shape of the resonant speech cavity and by making the usual tongue, teeth, and lip constrictions so as to articulate the modulated tone as human speech.

Many artificial larynxes include an electromechanical transducer for producing vibrations (i.e., the tone) and rechargeable batteries for power. Some artificial larynxes look like torch-shaped flashlights that the user holds and presses against the outside of the throat; vibrations travel through the throat tissues and into the mouth and throat. Another type of artificial larynx includes an oral tube which the user passes between the lips so that the tube extends directly into the mouth; vibrations travel through the tube and into the mouth. Still another type of artificial larynx includes a vibrating transducer that the user places directly in the mouth and operates with tung movements or a hand held controller; vibrations are produce right in the mouth.

Originally, artificial larynxes were made with a single switch offering a single frequency. This resulted in a monotone voice which could be difficult to understand. If a readily comprehensible voice is to be produced, the fluctuations in loudness and frequency (i.e., intonation) of normal voice production must be matched. These fluctuations vary widely, so that a large number of loudness and frequency parameters must be produced. While many existing artificial larynxes continue to operate with a single frequency switch, there have been several attempts to recreate the variations in frequency associated with natural voice intonation.

One common method for changing the frequency of an artificial larynx has been the use of multiple switches. The user chooses between different frequencies by activating the different switches through such means as thumb operated buttons or a rocker switch. Drawbacks to this method include the limited and distinct frequency options, increased speech aid size requirements for multiple switches, and the manual coordination required in moving from one switch to another. In practice, many users do not utilize more than one switch-controlled frequency, effectively resulting in a single-switch monotone voice.

Another technique has been to utilize a position-dependent adjustable resistor, such as a linear or rotary potentiometer, to provide a continuous range of frequency options. While this method does increase the number of useable frequencies, it also requires a significant degree of operational dexterity. In addition, small adjustable resistors often are not highly reliable and may also require a significant amount of space in the speech aid.

U.S. Pat. No. 4,993,071, invented by Peter Griebel and issued Feb. 12, 1991, describes an artificial larynx in which the frequency pulsates as a function of time, automatically changing voice tones for the user. This method does not, however, give the user control over his or her voice pattern. In use, this feature has been deactivated when distributed in some countries as the pre-determined frequency fluctuations do not match all language or speech patterns.

U.S. Pat. No. 4,039,756, invented by Richard Burtschi and issued Aug. 2, 1977, describes the use of manually operated switches used to select gradual upward or downward pitch change inflections. This type of artificial larynx may be operated utilizing multiple buttons, or a rocker switch. Disadvantages to this method are that it does not offer an extensive number of frequency options, does not easily allow specific word intonations, and requires the same high degree of manual coordination required by the above-mentioned multiple switch device.

SUMMARY OF THE INVENTION

This invention solves the problems outlined above by providing an ergonomically improved artificial larynx having control components that enable turn-on and frequency control with one pushbutton. A pressure-sensitive resistor is electrically connected in the circuit and physically disposed intermediate the pushbutton (or other suitable depressor component) and the associated switch actuator to enable one-button operation. Pressing the pushbutton applies force to the pressure-sensitive resistor as well as the switch actuator, to thereby enable both turn-on and frequency variation with minimal, unnoticeable movement of the thumb pressing the pushbutton.

To paraphrase some of the claim language that is subsequently presented, an artificial larynx constructed according to the invention includes a case and means in the form of an electrical circuit within the case for producing a tone having a frequency in the human voice range. The electrical circuit includes control means for enabling a user to turn on the electrical circuit and vary the frequency of the tone. The control means include a switch having a switch actuator for actuating the switch in response to the user applying force to the switch actuator. The switch also includes a button or other suitable depressor component for enabling the user to apply force to the switch actuator by pressing the depressor component.

According to a major aspect of the invention, the control means also includes a pressure-sensitive resistor (PSR) electrically connected in the circuit so that the frequency of the tone varies in response to the user applying force to the PSR. The PSR is physically disposed intermediate the depressor component and the switch actuator so that pressing the depressor component applies force to the pressure-sensitive resistor as well as the switch actuator, thereby enabling the user to turn on the electrical circuit and vary the frequency of the tone by operation of the depressor component. One embodiment includes remote volume control capabilities using an infrared or other suitable signal encoded with volume control information derived from a pressure sensor on the user's neck.

In line with the foregoing, the following are several objects and advantages of the invention:

a) Easy operation with single-button control over frequency;

b) A wide and continuous range of frequencies, allowing for increased control and subtle voice inflection options;

c) Reliability provided by the elimination of moving parts and PSRs rated for several million usage cycles;

d) Complete and immediately responsive control over frequency in response to force variations allows syllable specific intonation which may be used to approximate regional or country specific voice patterns;

e) Reduced coordination required for pressure-sensitive frequency variation which is not position dependent; and f) Compact PSRs allow for a small, convenient, artificial larynx.

The following illustrative drawings and detailed description make the foregoing and other objects, features, and advantages of the invention more apparent.

BRIEF DESCRIPTION OF THE DRAWINGS

FIG. 1 of the drawings is a perspective view of an artificial larynx constructed according to the invention;.

FIG. 2 is an enlarged cross sectional view taken on line 2—2 of FIG. 1;

FIG. 3 is a further enlarged cross sectional view taken on line 3—3 of FIG. 2;

FIG. 5 is a diagrammatic representation of the major components;

FIG. 6 is a diagrammatic representation similar to FIG. 5 of a second embodiment that includes remote volume control capabilities; and FIG. 7 is a cross sectional view similar to FIG. 3 of a portion of the second embodiment that illustrates placement of an infrared sensor device that is used in conjunction with other receiver components for receiving an infrared signal encoded with volume control information.

DESCRIPTION OF THE PREFERRED EMBODIMENTS

Figure 4:
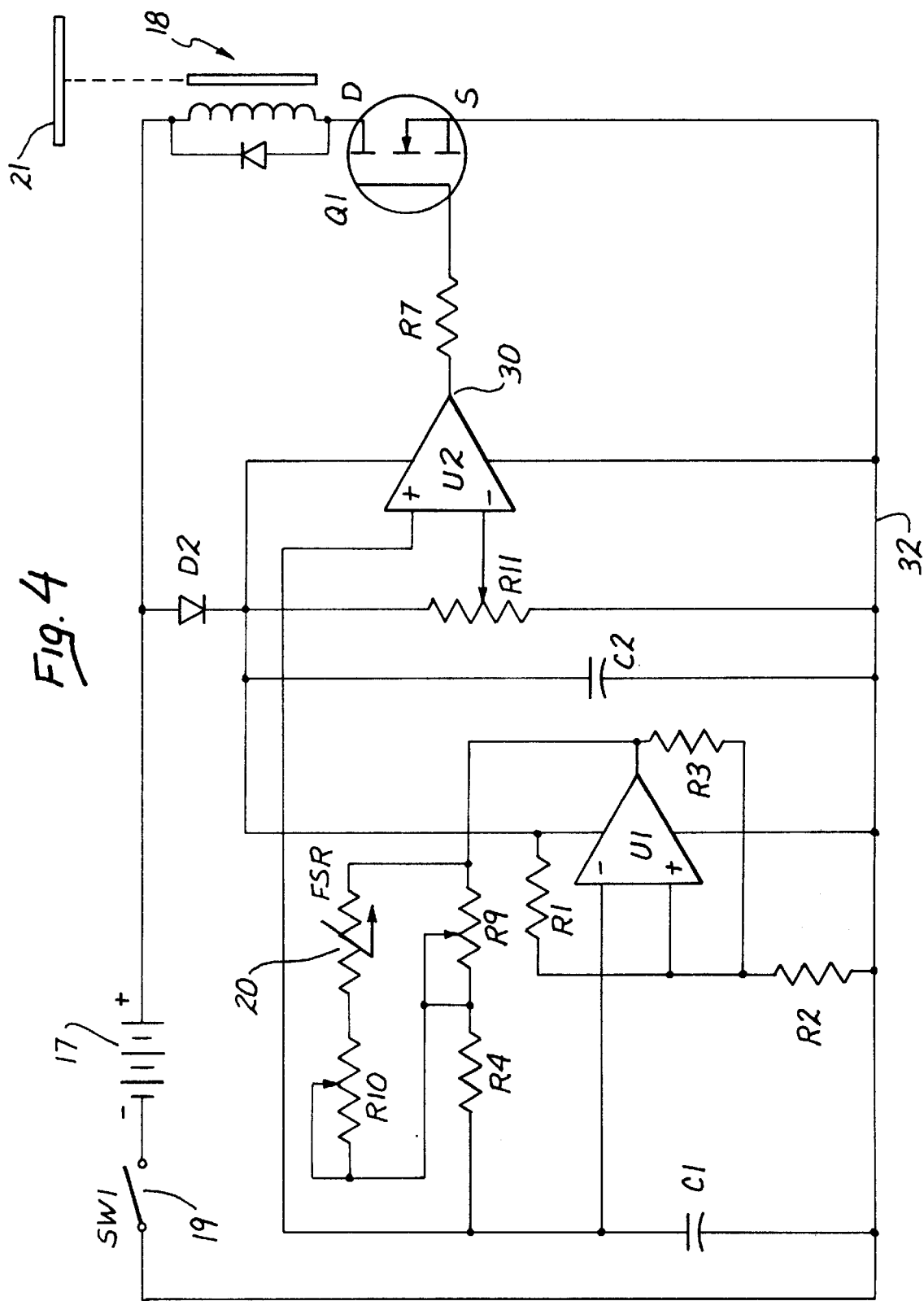
FIG. 4 is a schematic circuit diagram of the circuitry employed.

FIGS. 1–3 show various structural aspects of an artificial larynx 10 constructed according to the invention. Generally, the artificial larynx 10 includes a case 11 together with an electrical circuit and various associated components within the case 12. The case 12 may be similar in some respects to the cases used for existing artificial larynxes. It may be fabricated from any of various suitable materials (e.g., plastic or metal alloy), and it has a hollow interior 12, a proximal end portion 13, a distal end portion 14, and a midportion 15 (FIGS. 1 and 2). Preferably, the proximal and distal end portions 13 and 14 screw onto the midportion 15 to allow easy access to components within the interior 12.

As an idea of size, the illustrated case 11 measures about 4.0 to 4.5 inches long and the midportion 15 measures about 1.25 inches in diameter. With those dimensions, a user may easily grip the case 11 in one hand in order to hold it in a operative position against the exterior of the user's throat. Of course, dimensioning may vary without departing from the inventive concepts disclosed.

The case 11 contains an electrical circuit that will be described in greater detail later on with reference to FIG. 4. The electrical circuit is subsequently referred to as the circuit. The illustrated circuit produces a tone having a fundamental frequency in the range of about 40 Hertz up to about 200 Hertz, but a circuit with other frequency characteristics may be employed within the scope of the claims.

The circuit includes a circuit board 16 mounted within the midportion 15. The circuit board 16 is visible in FIG. 3. The circuit board 16 electrical interconnects various components, including a 9-volt battery 17 (FIG. 3) that fits within the proximal end portion 13 of the case 11, an electromechanical transducer 18 that is mounted within the distal end portion 14 of the case 11, and a switch 19 (FIGS. 2 and 3), a pressure-sensitive resistor 20 (FIGS. 2 and 3), and a volume control resistor R11 (FIG. 4) that are all mounted within the midportion 15 of the case 11. The volume control resistor R11 is not visible in FIGS. 1–3, but it is shown schematically in FIG. 4 and diagrammatically in FIG. 5.

The circuit board also interconnects various components that are mounted directly on the circuit board 16. Those components are not shown in FIG. 3 in order to keep FIG. 3 somewhat uncluttered, but they are included in the schematic circuit diagram in FIG. 4. Connections to the circuit-board 16 from the battery 17, the electromechanical transducer 18, and the switch 19 are also omitted in FIG. 3 for illustrative convenience.

The circuit serves the function of producing a tone by driving the electromechanical transducer 18 in a known way so that it causes a diaphragm 21 (FIGS. 1 and 3) of the electromechanical transducer 18 to vibrate. The tone has an audible fundamental frequency in the speech range of the average human voice. The user places the distal end portion 14 against the throat to couple that tone to the throat.

The circuit includes control means for enabling a user to selectively turn on the circuit and vary the frequency of the tone. The switch 19 functions as means for enabling the user to selectively turn on the circuit. With the case 11 grasped in one hand and the distal end portion 14 against the user's throat, the user applies force to a depressor component (e.g., the illustrated 0.4-inch diameter pushbutton or just button 22) by pressing the button 22 with the thumb of the hand used to hold the case 11. The button 22 extends from a user-accessible position on the exterior of the case 11, through the case 11 to the interior 12 where it is mechanically coupled via a first rubber pad 23, the pressure-sensitive resistor 20, and a second rubber pad 24, to a switch actuator 25 that is part of the switch 19.

In other words, the switch 19 includes the button 22, and the button 22 is mechanically coupled to the switch actuator 25 to enable the user to apply force to the switch actuator 25 by applying force to the button 22. The rubber pads 23 and 24 abut the pressure-sensitive resistor 20; they conform to and transmit force to the pressure-sensitive resistor 20 when the user presses the button 22. The switch actuator 25 functions as means for enabling the user to actuate the switch 20 by applying force to the switch actuator 25. In other words, the switch actuator actuates the switch in response to the user applying force to the switch actuator. Thus, applying force to the button 22 results in force being applied to the switch actuator 25. That, in turn, actuates the switch 20 to turn on the circuit.

The control means also includes the pressure-sensitive resistor 20. It is connected in the circuit so that the frequency of the tone varies in response to the user applying force to the pressure-sensitive resistor 20. In other words, it functions as means for enabling the user to vary the frequency of the tone by applying force to the pressure-sensitive resistor 20. The pressure-sensitive resistor 20 is a known type component that has a resistance value that varies according to the force applied to the resistor. It is commercially available from various sources, including Force Imaging Technologies of Chicago, Ill. and Interlink Electronics of Camarillo, Calif. With the pressure-sensitive resistor 20 disposed as illustrated in FIGS. 2 and 3, intermediate the button 22 and the switch actuator 25, it is in a position enabling the user to apply force to the switch actuator 25 and to the pressure-sensitive resistor 20 simultaneously by applying force to the button 22. Thus, this combination enables the user to turn on the electric circuit and vary the frequency of the tone, all with minimal, unnoticeable movement of the thumb pressing the button 22.

The preceding and subsequent descriptions enable one of ordinary skill in the art to make various changes without departing from the intended scope of the claims. The depressor component, for example, can take any of various forms other than the illustrated pushbutton 22, so long at it is some sort of structure that the user presses to transmit force to the switch actuator and to the pressure-sensitive resistor. The switch actuator can take various forms also. It can even be part of a membrane switch; for a membrane switch, the actuator includes the membrane structure to which force is applied.

In addition, one of ordinary skill can configure a remote sensor to act as a switch, as well as a frequency control, thereby eliminating the need for a mechanical switch. In other words, the sensor turns on the circuit at a predetermined voltage level, and as the voltage level increases, the frequency of the tone does also. That way of doing it takes advantage of lower failure rates of sensors compared to mechanical switches. These and many other variations are intended to fall within the scope of the claims.

Further details of the circuit are shown in FIG. 4. It includes first and second operational amplifiers U1 and U2 (e.g., a 1458 dual operational amplifier) that produce a rectangle wave signal at the output 30 of U2. Resistors R1 and R20 (e.g., 100k) bias the positive input of U1, a resistor R3 (e.g., 100k) provides feedback to the positive input of U1, and the combination of C1 (e.g., .33 microfarad), the pressure-sensitive resistor 20, and resistors R4, R9, and R10 (e.g., 10K, 50K, and 100k, respectively), provide feedback to the negative input of U1 to determine the frequency of the rectangle wave signal and thereby the frequency of the tone produced by the diaphragm 21 of the electromechanical transducer 18 (e.g., 84 turns of #38 wire on a suitable core).

The rectangle wave signal is couple to the positive input of U2 and then from U2 by a resistors R7 (e.g., 10K) to the gate of a MOSFET Q1 (e.g., IRFR024 or equivalent). The source of Q1 is connected to a common line 32 that the switch 19 connects to the negative terminal of the 9-volt battery 17 to turn on the circuit. In other words, when the user actuates the switch 19 by pressing the button 22 in FIGS. 1–3, the switch 19 connects the common line 32 in FIG. 4 to the negative terminal of the battery 17. Pressing the button 22 also applies force to the resistor 20 in FIG. 4, and that causes the frequency of the tone to vary.

A variable resistor R11 (e.g., 20K) connected to the negative input of U2 determines the amplification U2 to thereby function as a volume control. The user rotates a thumbwheel 31 illustrated in FIG. 1 to adjust the resistor R11, and to thereby adjust the volume of the tone produced by the diaphragm 21 of the electromechanical transducer 18. In other words, the circuit includes means for enabling the user to vary the volume of the tone, and the means for enabling the user to do so includes the thumbwheel 31.

The electromechanical transducer 18 is connected between the drain of Q1 and the positive terminal of the battery 17; Q1 drives the electromechanical transducer 18. A diode D2 protects against an inadvertent reverse battery connection. A capacitor C2 (e.g., 10 microfarad) filters the signal while providing protection against turn-on transients. Circuit particulars are well within the skill of one of ordinary skill in the art. One of ordinary skill in the art can choose suitable component values for the operation desired.

FIG. 5 is a simplified diagrammatic representation of the circuit and user controls extending through openings in the case 11. The button 22 extends through an opening 33 in the case 11 and the thumbwheel 31 extends through an opening 34. The one-headed arrow above the button 22 depicts the user pressing the button 22. The broken line between the button 22 and the resistor 20 depict transmission of force between the button 22 and the resistor 20 when the button 22 is pressed. Similarly, the broken line between the resistor 20 and the switch actuator 25 depict transmission of force between the resistor 20 and the actuator 25 when the button 22 is pressed.

The block 35 in FIG. 5 represents other circuit components of the electrical circuit not otherwise diagrammatically represented in FIG. 5, including the battery 17 and the electromechanical transducer 18. The double-headed arrow above the thumbwheel 31 depicts rotation of the thumbwheel 31. The broken line between the thumbwheel 31 and the volume control resistor R11 depicts mechanical coupling of the thumbwheel 31 to R11.

FIGS. 6 and 7 illustrate a second embodiment of an artificial larynx constructed according to the invention. It is designated generally by reference numeral 100. It is similar to the artificial larynx 10 in many respects, and so only differences are described in further detail. For convenience, references numerals designating parts of the artificial larynx 100 are increased by one hundred over those designating corresponding parts of the larynx 10.

Like the artificial larynx 10, the artificial larynx 100 includes a case 111 that is visible in both FIGS. 6 and 7, an electrical circuit within the case 111 that is represented in part by a box 135 in FIG. 6 and by a circuitboard 116, a battery 117, and a switch 119 in FIG. 7, together with a button 122 that is mounted in line with a pressure-sensitive resistor 120 and a switch actuator 125 (FIG. 7). But the artificial larynx 100 is different in that it includes means for enabling remote control of the volume of the tone the circuit produces. In other words, the user can control the volume by remote control with information transmitted to the circuit in the artificial larynx 100.

The means for enabling remote control of the volume includes a receiver circuit 140. It employs suitable circuitry, which may, for example, be coupled to the negative input of an operational amplifier corresponding to U2 in FIG. 4 (either with or without a resistor corresponding to R11). The circuitry employed in the receiver circuit 140 is adapted to receive volume information encoded on a signal transmitted to the receiver circuit 140. It produces a suitable control signal according to the volume control information received and couples that signal to the rest of the circuit to thereby control the volume according to the volume control information received.

From the preceding and subsequent descriptions, one of ordinary skill in the art can provide suitable circuitry for doing this. Any of various transmission, reception, and encoding methods may be used, including wire, radio, and infrared. The illustrated receiver circuit includes means in the form of an infrared sensor 141 extending through an opening 142 in the case 111. The sensor 141 receives an infrared signal on which at least one of on-off information, tone information, and volume information is encoded. Such an infrared signal is depicted in FIG. 6 as emanating from a transmitter 143 toward the sensor 141. The transmitter 143 encodes the signal with at least one of on-off information, tone information, and volume control information in response to a pressure sensor 144 placed proximate an opening in the user's throat through which the user exhales (e.g., a surgical opening called a stoma, but not limited to such an opening), according to the pressure sensed by the pressure sensor 144. Suitable pressure sensors for that purpose are commercially available from SenSyn of Milpitas, Calif.

Thus, the invention provides an ergonomically improved artificial larynx having control components that enable turn-on and frequency control with one pushbutton. An artificial larynx with a pressure-sensitive resistor connected to frequency control components in the circuit provides a reliable and easy to use method of frequency variation. Speech impaired people are able to speak with a more natural voice which includes the wide range of intonation capabilities found in normal human speech. The instantaneous changes in frequency created by varying degrees of pressure applied to the pressure-sensitive resistor allow the user to apply subtle degrees of intonation to specific words and syllables. By eliminating the position dependent frequency adjustment methods of the past, the invention allows an easier and more instinctual speaking fashion. In addition, compact and highly reliable pressure-sensitive resistors are available which eliminate the space requirements and reliability problems associated with prior methods of frequency variation.

Although an exemplary embodiment has been shown and described, one of ordinary skill in the art may make many changes, modifications, and substitutions without necessarily departing from the spirit and scope of the invention. For example, a pressure-sensitive resistor can be used with any of various other circuit configurations. A pressure-sensitive resistor can be used for volume control. Additionally, switch particulars can be changed without departing from the scope of the claims.

Another embodiment includes a circuit that is configured to enable the user to turn it on and off and vary the frequency by remote control (i.e., by information transmitted to the circuit). FIG. 6 is intended to illustrate that embodiment. The transmitter encodes on/off and frequency information according to pressure sensed by a sensor placed proximate the users throat where the user exhales. The transmitter transmits the information to the receiver. The receiver decodes the information and controls the circuit accordingly.

What is claimed is:

1. An artificial larynx, comprising:

a case; and an electrical circuit within the case for producing a tone having a frequency in the human voice range;

the electrical circuit including control means for enabling a user to turn on the electrical circuit and vary the frequency of the tone;

the control means including a switch, the switch having a switch actuator for actuating the switch in response to the user applying force to the switch actuator, and the switch further including a depressor component for enabling the user to apply force to the switch actuator by pressing the depressor component; and the control means also including a pressure-sensitive resistor electrically connected in the circuit so that the frequency of the tone varies in response to the user applying force to the pressure-sensitive resistor;

the pressure-sensitive resistor being physically disposed intermediate the depressor component and the switch actuator so that pressing the depressor component applies force to the pressure-sensitive resistor as well as the switch actuator, thereby enabling the user to turn on the electrical circuit and vary the frequency of the tone by operation of the depressor component.

2. An artificial larynx as recited in claim 1, wherein the electrical circuit includes means for enabling the user to vary the volume of the tone.

3. An artificial larynx as recited in claim 2, wherein the means for enabling the user to vary the volume of the tone includes a variable resistor having a thumbwheel control.

4. An artificial larynx as recited in claim 2, wherein the means for enabling the user to vary the volume of the tone includes means for enabling remote control of the volume.

5. An artificial larynx as recited in claim 4, wherein the means for enabling remote control of the volume includes means in the form of a receiver circuit adapted to receive volume information encoded on a signal transmitted to the receiver circuit.

6. An artificial larynx as recited in claim 5, wherein the receiver circuit includes an infrared sensor for receiving an infrared signal on which volume information is encoded.

7. An artificial larynx as recited in claim 1, wherein the depressor component includes a button extending from the exterior of the case to the interior of the case.

8. An artificial larynx as recited in claim 7, wherein the depressor component includes a first rubber pad intermediate the button and the pressure-sensitive resistor and a second rubber pad intermediate the pressure-sensitive resistor and the switch actuator.

9. A method for varying the frequency of a tone produced by an electrical circuit of an artificial larynx, comprising:

providing a pressure-sensitive resistor electrically connected in the electrical circuit and physically disposed intermediate a depressor component and a switch actuator, said pressure-sensitive resistor being electrically connected in the electrical circuit so that the frequency of the tone varies in response to the user applying force to the pressure-sensitive resistor, and said pressure-sensitive resistor being physically disposed intermediate the depressor component and the switch actuator so that pressing the depressor component applies force to the switch actuator to turn on the electrical circuit and so that pressing the depressor component also applies force to the pressure-sensitive resistor;

pressing the depressor component in order to apply force to the switch actuator and thereby turn on the electrical circuit; and varying the pressing of the depressor component in order to vary the force applied to the pressure-sensitive resistor and thereby vary the frequency of the tone.

* * * * *